United States Patent [19]

Lamanec et al.

[11] Patent Number: 4,870,080

[45] Date of Patent: Sep. 26, 1989

[54] POLYHYDRO DERIVATIVES OF 10,11-DIHYDRO-5H-DIBENZO[A,D]CYCLOHEPTEN-5,10-IMINE

[75] Inventors: Theresa R. Lamanec, Bricktown, N.J.; Terry A. Lyle, Lederach, Pa.

[73] Assignee: Merck & Co., Inc., Rahway, N.J.

[21] Appl. No.: 190,320

[22] Filed: May 5, 1988

Related U.S. Application Data

[63] Continuation-in-part of Ser. No. 83,114, Aug. 10, 1987, abandoned.

[51] Int. Cl.$^4$ .................. A61K 31/47; C07D 471/08
[52] U.S. Cl. ............................. 514/289; 546/72
[58] Field of Search .................. 546/72; 514/289

[56] References Cited

U.S. PATENT DOCUMENTS 3,812,119  5/1974  Walker ...................... 546/72 X
4,052,508  10/1972  Anderson et al. ............ 546/72 X

FOREIGN PATENT DOCUMENTS 1035141  1/1959  Fed. Rep. of Germany .
0461475  10/1968  Switzerland .

OTHER PUBLICATIONS

Lown et al., J. Org. Chem., vol. 36(10) (1971), pp. 1405–1413.

*Primary Examiner*—Mukund J. Shah
*Assistant Examiner*—Andrew G. Rozycki
*Attorney, Agent, or Firm*—William H. Nicholson; Joseph F. DiPrima

[57] ABSTRACT

10,11-Dihydro-5H-dibenzo[a,d] cyclohepten-5,10-imines and derivatives thereof wherein one or the other or both benzo rings are hydrogenated are active anticonvulsants and atagonists of N-methyl-D-aspartate.

11 Claims, No Drawings

POLYHYDRO DERIVATIVES OF 10,11-DIHYDRO-5H-DIBENZO[A,D]CYCLOHEPTEN-5,10-IMINE

This is a continuation-in-part of copending application Ser. No. 083,114, filed Aug. 10, 1987, now abandoned.

SUMMARY OF THE INVENTION

This invention is concerned with a compound of structural formula I:

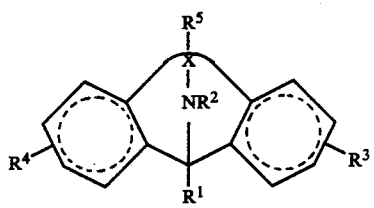

wherein X, $R^1$, $R^2$, $R^3$, $R^4$ and $R^5$ are as defined hereinafter and the dotted lines represent all degrees of saturation and unsaturation. The compounds represented thereby are useful as anticonvulsant agents and N-methyl-D-aspartate (NMDA) antagonists useful in the treatment of neuro-degenerative diseases.

The invention is also concerned with pharmaceutical compositions comprising one or more of the novel compounds represented by structural formula I and methods of treatment of convulsions and neuro-degenerative diseases by administration of a novel compound or pharmaceutical formulations thereof.

The invention is also concerned with novel processes for preparing the novel compounds.

BACKGROUND OF THE INVENTION

5-Methyl-10,11-dihydro-5H-dibenzo[a,d]cyclohepten-5,10-imine (MK-801) and many derivatives thereof are the subject of U.S. Pat. No. 4,399,141 of Anderson et al., the disclosure of which is incorporated herein by reference. The principle clinical utility of MK-801 has been shown to be anticonvulsant. It also has been reported to be an NMDA antagonist useful in the treatment of neuro-degenerative diseases such as Alzheimer's disease.

Now with the present invention there are provided hydrogenated MK-801 and derivatives. These new derivatives are also anticonvulsants and NMDA antagonists useful in the prevention and/or treatment of neuro-degeneration in pathological conditions such as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-pontocerebellar atrophy, anoxia such as from drowning, spinal cord injury and poisoning by exogenous NMDA poisons (e.g. some forms of lathyrism).

DETAILED DESCRIPTION OF THE INVENTION

The novel compounds of this invention are represented by structural formula I

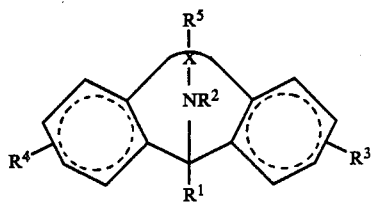

or a pharmaceutically acceptable salt thereof, wherein
X is a 1,2, or 3-carbon bridge and $R^5$ and $-NR^2$ are independently connected to one of the carbons of X.
$R^1$ is hydrogen, $C_{1-3}$ alkyl either unsubstituted or substituted with hydroxy;
$R^2$ is hydrogen, or $C_{1-3}$ alkyl;
$R^3$ and $R^4$ are independently hydrogen, $C_{1-3}$ alkoxy, hydroxy, or $C_{1-3}$ alkyl;
and $R^5$ is hydrogen, or hydroxy;
and the dotted circles independently represent benzo, tetrahydrobenzo or hexahydrobenzo rings with the proviso that they are not both benzo at the same time.

This invention contemplates all of the various sterochemical possibilities with respect to the ring fusions of the reduced ring to the central ring. For example, the possibilities for the compound described in Example 1 are as follows:

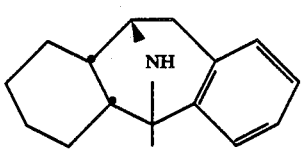

cis

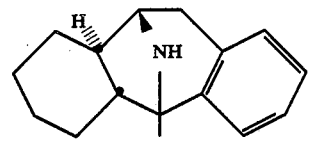

trans

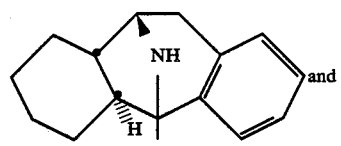

and trans

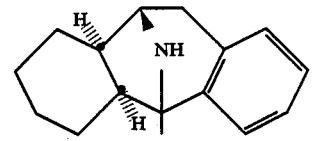

cis

For each reduced compound, similar possibilities exist, and are contemplated as part of this invention.

The novel compounds also can be resolved into their optical isomers by standard techniques, such as the formation of diastereomeric pairs by salt formation with an optically active acid, such as (—)-di-p-toluoyl-d-tartaric acid and/or (+)-di-p-toluoyl-1-tartaric acid followed by fractional crystallization and regeneration of the free base. The novel compounds may also be resolved by formation of diastereomeric esters or amides, followed by chromatographic separation and removal of the chiral auxiliary. The enantiomers and mixtures thereof are also within the scope of the present invention.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like.

In the anticonvulsant method of treatment aspect of the present invention, the novel imines of this invention are useful as anticonvulsants at a dosage level of from about 0.01 to about 20 mg per kilogram of body weight preferably about 0.05-2 mg/kg of body weight on a regimen of 1–4 times a day.

In the novel method of treatment of neuro-degeneration a dosage level of about 0.01 to 50 mg/kg, preferably about 0.05 to 10 mg/kg and especially about 0.05 to 0.5 mg/kg/day and may be administered on a regimen of 1 to 4 times per day.

It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a member of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The novel process for preparing compounds of structure

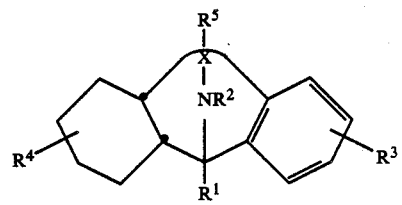

comprises treating the dibenzo-compound with rhodium chloride ($RhCl_3 \cdot 3H_2O$) in an ethanolic solution at about 15° to 40° C. for about 1 to 4 hours, followed by treatment with sodium borohydride ($NaBH_4$) at about 15° to 40° C. for about 1 to 5 hours.

Another novel process for preparing the above compound and other novel compounds comprises hydrogenating the dibenzo starting material with hydrogen, in ethanol in the presence of a rhodium on aluminum oxide ($Rh/Al_2O_3$) catalyst at about 40° to 70° C. starting at a pressure of about 500 to 1500 psi ($3.5 \times 10^5$ to $10.5 \times 10^5$ kg m$^{-2}$), for about 10 hours to 7 days or with Raney nickel at about 1500 psi and 1500° C. for about 12 to 24 hours or until hydrogen is no longer consumed, followed by removal of catalyst and chromatographic separation of the components of the reduction product.

An additional process comprises hydrogenation of a dibenzo starting material or an N-hydroxyl derivative thereof with 5% palladium-on-carbon at about 50°–100° C. and about 40 psi (195 kg m$^{-2}$) which is depicted as follows:

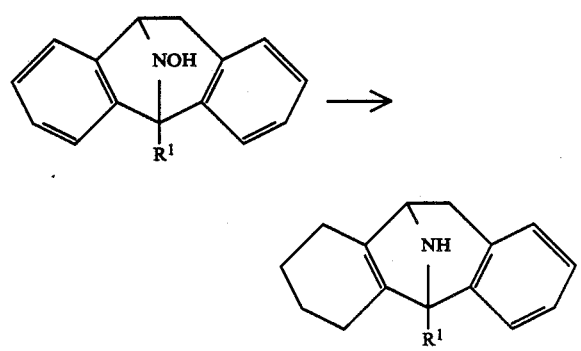

A Birch type reduction of MK-801 with Li wire in n-propylamine followed by chromatographic separation of the components provides:

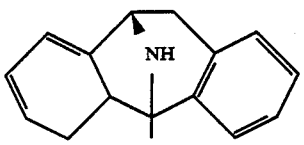

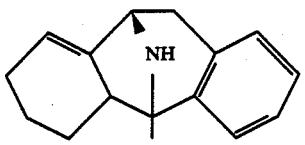

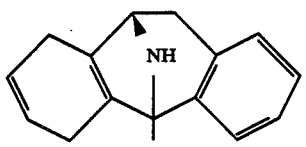

EXAMPLE 1

5R,5aS,9aR,10R-5a,6,7,8,9,9a,10,11-Octahydro-5-methyl-5H-dibenzo[a,d]cyclohepten-5,10-imine

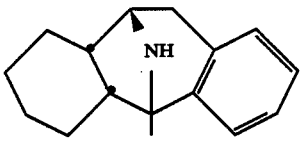

A suspension of 3.0 g (8.89 mmol) of MK-801 in 200 mL of CHCl₃ was washed with 10% NaHCO₃, dried over Na₂SO₄, and evaporated to give the free base which was dissolved in 20 mL of C₂H₅OH and evaporated twice to remove traces of CHCl₃. This free base was dissolved in 200 mL of C₂H₅OH, and 2.36 g (8.98 mmol) of RhCl₃·3H₂O was added in one portion. After stirring under N₂ at 30° for 1.5 hours, a solution of 3.36 g (88.9 mmol) of NaBH₄ in 200 mL of C₂H₅OH was added over a period of 3.0 hours. After stirring overnight at room temperature, the mixture was filtered through a Celite pad, washed with C₂H₅OH, and evaporated to a small volume at reduced pressure. The remaining NaBH₄ was carefully quenched by the addition of 200 mL of 2.5% HCl. After basifying with 2.0M NaOH, the aqueous solution was extracted with 2×250 mL of CHCl₃, the combined organics washed with saturated NaHCO₃, H₂O, brine, and dried over Na₂SO₄. The residue remaining after evaporation at reduced pressure was chromatographed on fine SiO₂ using 95:5:0.5 CHCl₃—CH₃OH—NH₄OH to give 1.25 g (62%) of the title compound as a colorless solid. mp=56°–58° C.

¹H NMR (CDCl₃): δ 0.41 (dq, 5, 12 Hz, H$_{6a}$), 0.92 (dq, 5, 12 Hz, H$_{9a}$), 1.15–1.55 (m, 6H), 1.57 (s, H₃C), 1.92 (dt, 5.5, 11 Hz, H$_{5a}$), 2.27 (s, H—N), 2.35 (dddd, 5, 7, 11, 12 Hz, H$_{9a}$), 2.75 (d, 17 Hz, H$_{11\beta}$), 3.07 (dd, 5.5, 17 Hz, H$_{11\alpha}$), 3.80 (ddd, 5.5, 7, 1 Hz, H$_{10}$), 7.00–7.18 (m, 4H-arom).

R$_f$=0.4 (90:10:1 CHCl₃—CH₃OH—NH₄OH).

[α]$_D$=−20.3 (c=1.15, CH₃OH).

A solution of the free base in ether was treated with ethanolic HCl to give the HCl salt: mp=233–235 dec.

The maleate salt has m.p. 149°–150° C.; [α]$_D$=−5.24 (c=1.17 CH₃OH).

Calc'd for C₁₆H₂₁N·C₄H₄O₄: C 69:95; H, 7.34; H, 4.08. Found C 16.65; H, 7.13; N, 4.07.

The following compounds were prepared using the procedure substantially as described in Example 1, but in each case starting with the corresponding dibenzo compound.

5a,6,7,8,9,9a,10,11-octahydro-10-hydroxy-5-(2-hydroxyethyl)-5H-dibenzo[a,d]cyclohepten-5,10-imine

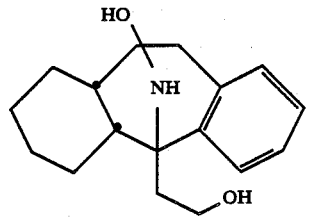

Purified by chromatography on silica gel using 95:5:0.5 CHC₃—CH₃OH—NH₄OH and trituration with 1:1 hexane-acetonitrile: mp=169°–171° C.

Calc'd for C₁₇H₂₃NO₂ C 74.69; H 8.48; N 5.12. Found: C 74.33; H 8.42; N 4.94.

5a,6,7,8,9,9a,10,11-octahydro-11-exo-hydroxy-5-methyl-5H-dibenzo[a,b]cyclo-hepten-5,10-imine

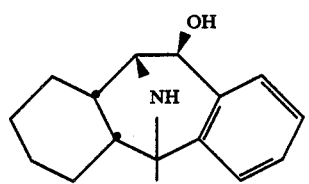

Purified by silica gel chromatography using 90:10:1.0 CHC₁₃—CH₃OH—NH₄OH. Maleate salt prepared by sissolving the free base in warm ethyl acetate and adding maleic acid: [α]$_D$=+11.89 (c=0.56 CH₃OH). Calc'd for C₁₆H₂₁NO·C₄H₄O₄ C 66.87; H 7.01; N 3.90. Found: C 66.56; H 7.39; N 3.88.

5a,6,7,8,9,9a,10,11-octahydro-5-methyl-5H-dibenzo[a,d]cycloocten-5,11-imine

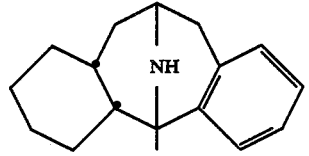

Calc'd for C₁₇H₂₃N C 84.58; H 9.60; N 5.80. Found C 84.50; H 9.87; N 5.67.

1,2,3,4,4a,9,10,10a-octahydro-N,9,10-trimethylanthracen-9,10-imine

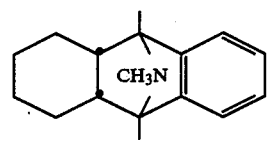

Purified by silica gel chromatography using 95:5:5:0 CHC₃—CH₃OH—NH₄OH. Prepared HCl salt by dissolving the free base in ether and adding ethanolic HCl:

Calc'd for C₁₇H₂₃N HCl.0.2 H20: C 72.55; H 8.74; N 4.98. Found: C 72.62; H 9.03; N 4.97.

(+) 5R,5aS,9aR,10R-5a,6,7,8,9,9a,10,11-Octahydro-N,5-dimethyl-5H-dibenzo[a,d]cyclohepten-5,10-imine

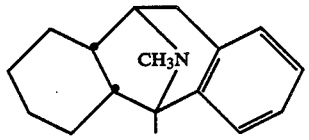

Purified by silica gel chromatography using 95:5:0.5 CHC₃—CH₃OH—NH₄OH. Prepared HCl salt by dissolving free base in ether and adding ethanolic HCl:

[α]D = +12.3 (c=0.64 CH3OH).

Calc'd for C₁₇H₂₃N.HCl.0.4 H 20: C 71.63; H 8.77; N 4.91. Found C 71.64; H 8.80; N 5.01.

5R,5aS,9aR,10R-5a,6,7,8,9,9a,10,11-Octahydro-5-(2-hydroxyethyl)-5H-dibenzo[a,d]cyclohepten-5,10-imine

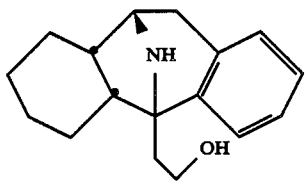

Purified by silica gel chromatography using 90:10:1.0 CHC₃—CH₃OH—NH₄OH.

Calc'd for C₁₇H₂₃NO: C 76.65; H 9.08; N 5.25. Found: C 76.31; H 8.99; N 5.24.

EXAMPLE 2

High Pressure Hydrogenation of (±) 10,11-Dihydro-5-methyl-5H-dibenzo[a,d]cyclohepten-5,10-imine acetate salt A solution of 220 mg (0.782 mmol) of the title compound in 10 mL of ethanol was hydrogenated over 40 mg of 5% Rh/Al₂O₃ at 1000 psi at 60° C. overnight.

The reaction mixture was filtered, poured into 5% NaHCO₃, extracted with two portions of CHCl₃, dried over Na₂SO₄, and the solvents removed at reduced pressure. The brown residue was chromatographed on 25 g of fine silica gel using the following solvents: 95:5:0.5 CHCl₃—CH₃OH—NH₄OH (150 ml), 92.5:7.5:0.75 (100 mL), 90:10:1 (100 mL) and 87.5:12.5:1.25 (100 mL). The 3 mL fractions were analyzed by TLC (SiO₂), combined and evaporated at reduced pressure as follows:

Fractions 29–37 provided 5 mg of 1,2,3,4,10,11,-Hexahydro-5-methyl-5H-dibenzo[a,d]cyclohepten-5,10-imine.

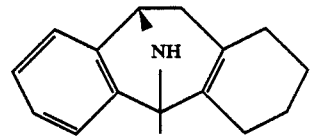

¹H NMR (CDCl₃): δ 1.14–1.98 (m, 9H), 1.52 (S, H₃C), 2.10–2.25 (m, 1H), 2.52 (brs, H—N), 2.65 (dm, 17 Hz, H₁₁), 4.45 (d, 5.5 Hz, H₁₀), 7.0–7.31 (m, 4 H-arom). R_f=0.52 (90:10:1 CHCl₃—CH₃OH—NH₄OH).

Fractions 46–76 provided 37 mg of a 1:1 mixture of 5R*,5aS*,9aR*,10R*-5a,6,7,8,9,9a,10,11-Octahydro-5-methyl-5H-dibenzo[a,d]cyclohepten-5,10-imine

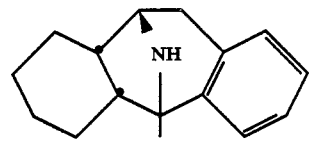

¹H NMR (CDCl₃): δ 0.41 (dq, 5 12 Hz, H₆α), 0.92 (dq, 5, 12 Hz, H₉α), 1.15–1.55 (m, 6H), 1.57 (s, H₃C), 1.92 (dt, 5.5, 11 Hz, H₅ₐ), 2.27 (S, H—N), 2.35 (dddd, 5,7,11,12 Hz, H₉ₐ), 2.75 (d, 17 Hz, H₁₁β), 3.07 (dd, 5.5, 17 Hz, H₁₁α), 3.80 (ddd, 5.5, 7, 1, Hz, H₁₀), 7.00–7.18 (m, 4 H-arom). R_f=0.4 (90:10:1 CHCl₃—CH₃OH—NH₄OH). mp=58°–60° C. and 4aR*,5S*,10R*,11aR*-1,2,3,4,4a,10,11,11a-Octahydro-5-methyl-5H-dibenzo[a,d]cyclohepten-5,10-imine

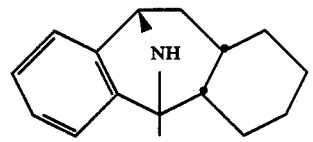

¹H NMR (CDCl₃): δ −0.185 (dq, 4, 12 Hz), 1.50 (s, H₃C), 2.18 (m, 1H), 4.24 (dd, 2.4, 3.9 Hz, H₁₀), 7.0–7.2 (m, 4, H-arom).

R_f=0.4 (90:10:1 CHCl₃—CH₃OH—NH₄OH).

Fractions 124–130 provided 7 mg of 5S*,5aS*,9aR*,10R*-1,2,3,4,5a,6,7,8,9,9a,10,11,-Dodecadecahydro-5-methyl-5H-dibenzo[a,d]cyclohepten-5,10-imine

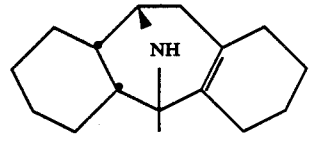

¹H NMR (CDCL₃): δ 1.1–1.6 (m, 8H), 1.49 (s, H₃C), 1.6–2.1 (m, 9H), 2.14 (dt, 5, 12 Hz, 1H), 2.44–2.68 (m, 2H), 3.96 (dd, 2, 5 Hz, H₁₀), 6.77 (brs, H—N). R_f=0.18 (90:10:1 CHCl₃—CH₃OH—NH₄OH).

EXAMPLE 3

High Pressure Hydrogenation of (±)10,11-Dihydro-5-methyl-5H-dibenzo[a,d]cyclohepten-5,10-imine acetate salt A solution of 4.1 g (14.6 mmol) of the title compound in 150 mL of ethanol was hydrogenated over 1.25 g of 5% Rh/A12O3 at 1500 psi 60° C. for 18 h. The reaction mixture was filtered and the solvents removed at reduced pressure. The brown residue was chromatographed on 400 g of fine silica gel using the following solvents: 95:5:0.5 CHC13—CH3OH—NH4OH [2 L], 92.5:7.5:0.75) 1.5 L), 90:10:1 (1.5 L) and 87.5:12.5:1.25 (1 L). The 24 mL fractions were analyzed by TLC (SiO2), combined and evaporated at reduced pressure as follows:

Fractions 49-52, 76 mg of:

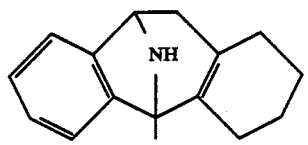

1,2,3,4,10,11-Hexahydro-5-methyl-5H-dibenzo[a,d]cyclohepten-5,10-imine

1H NMR (CDC13): δ 1.14-2.09 (m, 11H), 1.50 (s, H3C), 2.10-2.25(m, 1H), 2.65(dm, 17 Hz, H11), 4.45(d, 5.5 Hz, H10), 7.0-7.3(1 m, 4 H-arom). R$_f$=0.52 (90:10:1 CHC13—CH3OH—NH4OH).

The HCl salt was prepared in 1:1 ether-pentane using ethanolic HCl.

Calc'd for C16H19N, HCl0.01 H2O: C 72.91; H 7.72; N 5.31. Found: C 72.92; H 7.62; N 5.22.

Fractions 70-115, 760 mg of a mixture of compounds which were separated by acetylating in 10 mL of CH2C12 using 2 mL each of acetic anhydride and pyridine overnight. The reaction mixture was poured into 2M HCl and extracted with CHC3. After washing with H2O, drying over Na2SO4 and evaporation, the mixture of acetylated compounds was separated by preparative HPLC using a 70:30 to 35:65 gradient of 0.1% TFA in H2O—CH3CN over 1 h. The early eluting peak was collected, evaporated, and extracted with two portions of CHC3 to give 300 mg of a pure acetylated compound. This material was treated in two portions by dissolving in 10 mL of ethylene glycol and heating to 190° C. with 1.0 g of KOH for 5 h. The reaction mixture was poured into water and extracted with ether. The organic layer was washed with water, brine, dried over Na2SO4, and evaporated to give a residue which was chromatographed on 25 g of fine SiO2 using 93:7:0.7 CHC13—CH3OH—NH4OH to afford 135 mg of a colorless oil:

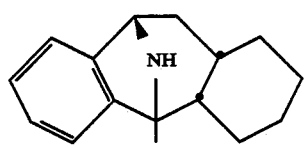

4aR*,5S*,10R*,11aR*-1,2,3,4,4a,10,11,11a-Octahydro-5-methyl-5H-dibenzo[a,d]cyclohepten-5,10-imine 1H NMR (CDC13): δ −0.185(dq, 4, 12 Hz), 1.48(s, H3C), 2.18(m, 1H), 4.24(dd, 2,4,3.9 Hz, H10), 7.0-7.2(m, 4H-arom). R$_f$=0.4(90:10:1 CHC13—CH3OH—NH4OH).

Calc'd for C16H21N.HCl: C 72.85; H 8.41; N 5.31. Found: C 72.40; H 8.27; N 5.43.

Fractions 161-171,62 mg of:

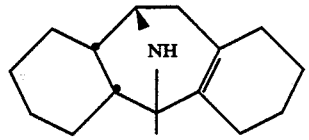

1,2,3,4,5a,6,7,8,9,9a,10,11-Dodecahydro-5-methyl-5H-dibenzo[a,d]cyclohepten-5,10-imine 1H NMR(CDC13): δ 1.1-1.45(m, 8H), 1.21(s, H3C), 1.62.1(m, 11H), 2.14-2.26 (m, 2H), 3.55(ddd, 2.5.7 Hz, H10).

R$_f$=0.18(90:10:1 CHC13—CH3OH—NH4OH).

The HCl salt was prepared in 1:1 ether-pentane using ethanolic HCl

Calc'd for C16H25N.HCl: C 71.75; H 9.78; N 5.23. Found: C 71.51; H 9.77; N 5.13.

EXAMPLE 4

Alternative High Pressure Hydrogenation of (+) 10,11-Dihydro-5-methyl-5H-dibenzo[a,d]cyclohepten-5,10-imine acetate salt A solution of 4.0 g(14.6 mmol) of the title compound in 150 mL of ethanol was hydrogenated over 1.0 g of Raney-Nickel at 1500° C. for 18 h. The reaction mixture was filtered and the solvents removed at reduced pressure. The brown residue was partitioned between CHC3 and 1% NaOH, and the organic layer was washed with water, dried over Na2SO4, and evaporated to give 2.51 g of an amber colored oil. This oil was chromatographed on 250 g of fine silica gel using the following solvents: 97:3:0.3 CHC13—CH3OH—NH4OH(0.5 L), 95:5:0.5 CHC13—CH3OH—NH4OH(0.5 L), 92,5:7.5:0.75 (O5 L), 90:10:1 (0.5 L) and 87.5:12:5:1.25 (1 L). The 24 mL fractions were analyzed by TLC (SiO2), combined and evaporated at reduced pressure as follows: Fractions 136-145, 450 mg of:

1,2,3,4,5a,6,7,8,9,9a,10,11-Dodecahydro-5-methyl-5H-dibenzo[a,d]cyclohepten-5,10-imine (described above)

Fractions 152-162, 556 mg of:

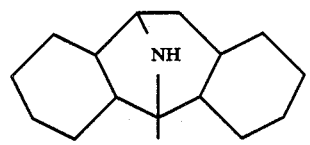

1,2,3,4,4a,5a,6,7,8,9,9a,10,11,11a-Tetrahydrodecahydro-5-methyl-5H-dibenzo[a,d]cyclohepten-5,10-imine The HCl salt was prepared in ether-pentane using ethanolic HCl:

Calc'd for C16H27N.HCl: C 71.21; H 10.46; N 5.19. Found: C 71.14; H 10.72; N 5.18.

EXAMPLE 5

Birch type reductions of MK-801

A solution of 1.0 g (4.52 mmol) of the free base of MK-801 in 50 mL of n-propylamine was cooled to 0° C. under N2, and 144 mg (20.7 g-atom) of Li wire was added in small pieces over 3 hours. The residual metal was removed, and the reaction quenched by the addition of 30 mL of sat. NH4Cl solution. The reaction mixture was extracted with three portions of ether, and the combined either layers washed with two portions of sat. NH₄Cl, water, and brine. After drying over MgSO₄, the solvents were removed at reduced pressure to give a reddish oil which was chromatographed on 100 g of fine SiO₂ using 98:2:0.2 CHCl₃—CH₃OH—NH₄OH taking 5 mL fractions. Fractions 50–62 were combined to give 107 mg of an orange oil. This oil was further purified by preparative reversed phase HPLC using a C-18 column with 0.1% trifluoroacetic acid in water and acetonitrile. The pure fractions were concentrated, basified, extracted, and evaporated to give an oil which was dissolved in ether and treated with 31 μL of 8.55 ethanolic HCl to afford 26 mg of a light brown solid:

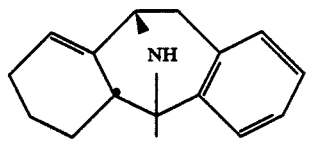

5a,6,7,8,10,11-hexahydro-5-methyl-5H-dibenzo[a,d]cyclohepten-5,10-imine hydrochloride salt

[a]$_D$=48.4 (c=0.43CH₃OH).
Calc'd for C₁₆H₁₉N.HCl 0.25 H₂0; C 72.17; H 7.76; N 5.26. Found: C 72.07; H 7.58; N 5.13.

Fractions 80–126 were combined and purified as described above to give 36 mg of a tan solid:

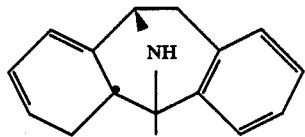

5a,6,10,11-Tetrahydro-5-methyl-5H-dibenzo[a,d]cyclohepten-5,10-imine hydrochloride salt

[a]$_D$=129 (c=0.35 CH₃OH).
Calc'd for C₁₆H₁₇N.HCl.0.4H₂O: C 71.98; H 7.09; N 5.24. Found C 72.17; H 6.97; N 4.86.

EXAMPLE 6

6,9,10,11-Tetrahydro-5-methyl-5H-dibenzo[a,d]cyclocyclohepten-5,10-imine

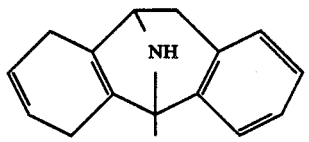

A stirred solution of 1.96 g (8.89 mmol) of MK-801 free base of 100 mL of n-propylamine and 2.4 mL of isopropanol under N₂ was cooled in an ice bath, and 315 mg of Li wire (washed with hexane, ethanol, and ether) was added in small pieces over 2.0 h. After stirring for 3.0 h in the cold, an additional 1.0 mL of isopropanol was added and stirring continued for 45 minutes. The reaction was quenched by the dropwise addition of sat. NH₄Cl to give a yellow solution. Most of the solvent was removed by evaporation in vacuo, and the aqueous residue was extracted with two portions of ether. The combined organic layers were washed twice with water, dried over Na₂SO₄, and the solvents removed by evaporation in vacuo to give a yellow oil which was chromatographed on 200 g of fine SiO₂ using 98:2:0.2 to 95:5:0.5 CHCl₃—CH₃OH—NH₄OH. Fractions containing the product were combined and evaporated in vacuo to give an oil which was purified by RP-HPLC using a Waters Delta-Pak C18 column and a gradient elution of 100%A to 55%A-45%B over 1 h. The fractions were assayed by HPLC, combined, and evaporated in vacuo to remove the acetonitrile. The aqueous residue was basified with 10% Na₂CO₃, extracted with three portions of CHCl₃, and the combined organic layers were washed with water, dried over Na₂SO₄, and the solvents removed to give 60 mg of a colorless oil: NMR. This oil was dissolved in ether and treated with ethanolic HCl to give 47 mg of a colorless solid: mp [a]D= =+146(c=0.42, CH₃OH).
Calc'd for C₁₆H₁₇N.HCl.0.2H₂O: C 72.1; H 7.05; N 5.30. Found: C 72.91; H 6.84; N 5.29.

EXAMPLE 7

7-Methoxy 1,2,3,4,4a,10,11,11a-octahydro-5-methyl-5H-dibenzo[a,d]cyclohepten-5,10-imine hydrochloride

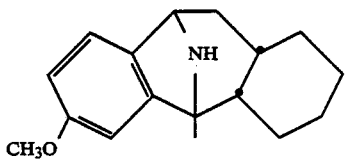

A mixture of 200 mg (0.795 mmole) of 7-methoxy-10,11-dihydro-5H-dibenzo[a,d]cyclohepten-5,10-imine and 420 mg (1.59 mmole) of rhodium (III) chloride trihydrate in 15 ml ethanol was stirred under nitrogen at 30° for 2.5 hr after which the red-brown suspension was treated over 1 hr with a solution of sodium borohydride (300 mg, 7.95 mmole) in 15 ml ethanol. Stirring at 25°–30° was continued for 18 hr. The mixture was filter through a pad of celite, the black solid washed with ethanol, and the filtrate concentrated on a rotary evaporator. The residue was treated with 10 g crushed ice, acidified with 3N HCl, and stirred at ambient temperature for 1 hr. Additional metallic solids were removed by filtration and the filtrate was brought up to pH 10 with NH₄OH. Extraction with ethylacetate, followed by washing with sat'd. NaHCO₃, water, and brine led to isolation of 179 mg of a yellow oil which was separated by flash chromatography, elution with CHCl₃/CH₃OH/NH₄OH (95:5:0.5 to 90:10:1). Thus were obtained 41 mg of unreacted starting material and 121 mg of title compound. The hydrochloride salt of the title compound was prepared from an ether-ethanol mixture, using ethanolic HCl for the acidification: m.p. 240°–242° dec, The ring-fusion sterechemistry at 4a,11a is cis-. For C₁₇H₂₃NO—HCl:
Anal. Calc'd.: N, 4.77; C, 69.49; H, 8.23. Found: N, 4.78; C, 69.65; H, 8.11.

EXAMPLE 8

7-Hydroxy 1,2,3,4,4a,10,11,11a-octahydro-5-methyl-5H-dibenzo[a,d]cyclohepten-5,10-imine hydrochloride

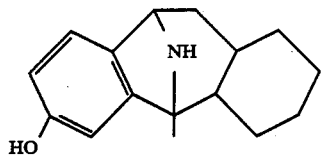

7-Hydroxy-10,11-dihydro-5-methyl-5H-dibeno-[a,d-]cyclohepten-5,10-imine (1.0 g, 4.2 mmole), was hydrogenated at 50° C., 1000 psi of $H_2$ with 0.5 g of 5% $Rh/A_{12}O_3$ catalyst for 5 days. The catalyst was removed by filtration through celite, the solids washed with 95% ethanol and the combined filtrates evaporated to afford 1.1 g of an oil which contained no starting material by TLC. The crude mixture was then dissolved in 35 ml THF and treated with 3.9 g of diterbutyldicarbonate and 35 ml of 1.0N NaOH. After stirring under nitrogen at 50° for 3 hr and 25° for 24 hr the layers were separated, the aqueous phase extracted thrice with ether, and the combined ether layers washed with water, then brine. Upon drying ($Na_2SO_4$), the solvent was removed and the residual oil chromatographed on silica gel, eluting with ethylacetate/hexane mixtures (from 40/60 to 50/50). The least polar fraction, accounnting for 67% of the recovered material, was dissolved in 60 ml $CH_2C_{12}$ and treated with 10 ml trifluoroacetic acid. After stirring under nitrogen at 25° for 2 hr the solution was evaporated to dryness and the residue was extracted into $CHC_{13}$ under alkaline conditions (aq. $Na_2Co_3$). Removal of the solvent left a brown solid which was purified by flash chromatography ($CHC_{13}$—$CH_3OH$—$NH_4OH$ 90/10/1) to give an oil, the PMR data of which supported the title compound. The oil was converted to a crystalline hydrochloride salt using standard methodology. For $C_{16}H_{21}NO$—HCl Anal. Calc'd.: N, 5.00; C, 68.68; H, 7.92. Found: N, 5.02; C, 68.50; H, 8.21.

EXAMPLE 9

Preparation of Intravenous Solutions

A solution containing 10 mg of a novel compound per mL of injectable solution is prepared in the following manner.

A mixture of 10 mg of active ingredient and 9 mg of sodium chloride is dissolved in sufficient water for injection to make 1 mL of solution. The pH is adjusted using hydrochloric acid or aqueous sodium hydroxide to about pH 7.0.

If it is desired that the intravenous solution be used for multi-dose purposes. 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg, respectively, of active ingredient per mL of solution are similarly prepared substituting the indicated amount for the above-illustrated 10 mg quantity. Bulk injectable solutions of convenient volume for subsequent delivery in unit dosage form are readily prepared following the above procedure.

EXAMPLE 10

Tablet Preparation

Tablets containing 1.0, 2.0, 25.0, 26.0, 50.0 and 100.0 mg, respectively, of active compound are prepared as illustrated below.

| TABLE FOR DOSES CONTAINING FROM 1-25 MG OF THE ACTIVE COMPOUND | | | |
|---|---|---|---|
| | Amount - mg | | |
| Active compound | 1.0 | 2.0 | 25.0 |
| Microcrystalline cellulose | 49.25 | 48.75 | 37.25 |
| Modified food corn starch | 49.25 | 48.75 | 37.25 |
| Maqnesium stearate | 0.50 | 0.50 | 0.50 |

| TABLE FOR DOSES CONTAINING FROM 26-200 MG OF THE ACTIVE COMPOUND | | | |
|---|---|---|---|
| | Amount - mg | | |
| Active compound | 26.0 | 50.0 | 100.0 |
| Microcrystalline cellulose | 25.0 | 100.0 | 100.0 |
| Modified food corn starch | 2.21 | 4.25 | 8.5 |
| Magnesium stearate | .39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet. Other tablets are prepared using the same procedures and the equivalent amounts of excipients along with equivalent amounts of any of the novel compounds of the present invention.

What is claimed is:

1. A compound of structural formula:

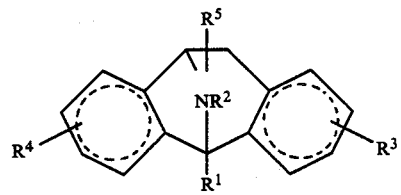

or a pharmaceutically acceptable salt thereof, wherein
$R^1$ is hydrogen, $C_{1-3}$ alkyl either unsubstituted or substituted with hydroxy;
$R^2$ is hydrogen or $C_{1-3}$ alkyl;
$R^3$ and $R^4$ are independently hydrogen;
$C_{1-3}$ alkoxy, hydroxy or $C_{1-3}$ alkyl;
$R^5$ is hydrogen or hydroxy;
and the dotted circles independently represent benzo, tetrahydrobenzo or hexahydrobenzo rings with the proviso that they are not both benzo at the same time.

2. The compound of claim 1 of structural formula:

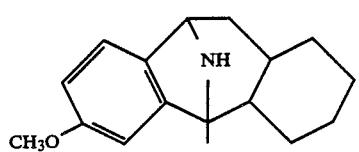

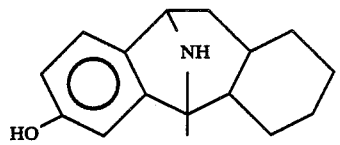

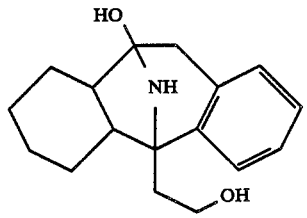

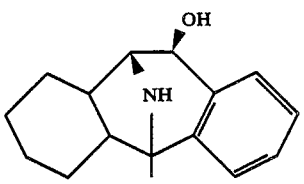

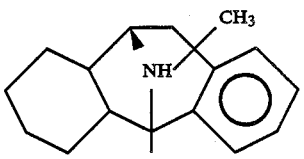

or

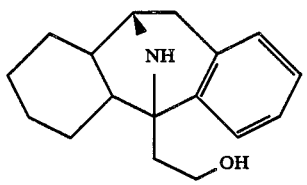

3. A compound of claim 1 with the structural formula:

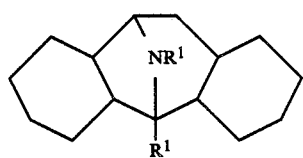

Ib or a pharmaceutically acceptable salt thereof, wherein R$^1$ is
  (1) —H,
  (2) —CH$_3$ or
  (3) —CH$_2$CH$_3$.

4. The compound of claim 3 of structural formula:

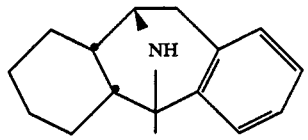

5. The compound of claim 3 of structural formula:

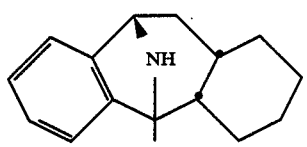

6. The compound of claim 3 of structural formula:

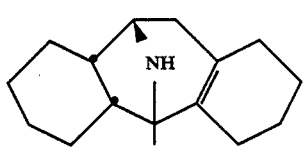

7. The compound of claim 3 of structural formula:

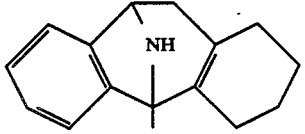

or

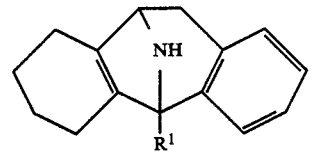

8. The compound of claim 1, of structural formula:

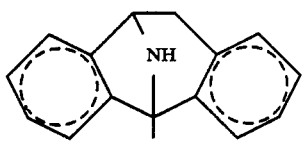

9. The compound of claim 8 of structural formula:

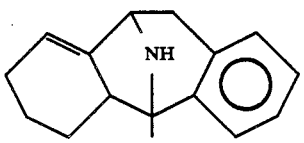

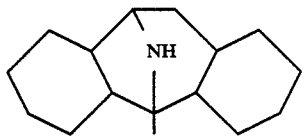

-continued

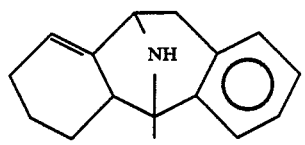

or

-continued

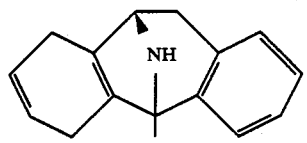

10. A pharmaceutical composition comprising a pharmaceutical carrier and an effective anticonvulsant amount of the compound of claim 1, or a pharmaceutically acceptable salt thereof.

11. A method of treating convulsions which comprises the administration to a patient in need of such treatment of an effective anticonvulsant amount of the compound of claim 1, or a pharmaceutically acceptable salt thereof.

* * * * *

UNITED STATES PATENT AND TRADEMARK OFFICE
CERTIFICATE OF CORRECTION

PATENT NO. : 4,870,080

DATED : September 26, 1989

INVENTOR(S) : T. R. Lamanec, et al

It is certified that error appears in the above-identified patent and that said Letters Patent is hereby corrected as shown below:

The chemical structure in Claim 3 should be:

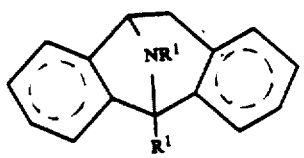

Signed and Sealed this

Ninth Day of October, 1990

Attest:

HARRY F. MANBECK, JR.

Attesting Officer      Commissioner of Patents and Trademarks